(12) United States Patent
Walker et al.

(10) Patent No.: US 8,628,536 B2
(45) Date of Patent: Jan. 14, 2014

(54) BIOLOGICS DELIVERY SYSTEM

(75) Inventors: Brandon T. Walker, Layton, UT (US);
Joseph Q. Marietta, Hyde Park, UT (US); Daniel E. Gerbec, Logan, UT (US); Douglas M. Lorang, North Logan, UT (US); Harold Linville, Tipp City, OH (US)

(73) Assignee: IMDS Corporation, Providence, UT (US)

(*) Notice: Subject to any disclaimer, the term of this patent is extended or adjusted under 35 U.S.C. 154(b) by 219 days.

(21) Appl. No.: 13/041,580

(22) Filed: Mar. 7, 2011

(65) Prior Publication Data

US 2011/0218513 A1    Sep. 8, 2011

Related U.S. Application Data

(60) Provisional application No. 61/311,044, filed on Mar. 5, 2010, provisional application No. 61/389,626, filed on Oct. 4, 2010.

(51) Int. Cl.
*A61B 17/56* (2006.01)
*A61M 5/00* (2006.01)
*G01F 11/00* (2006.01)

(52) U.S. Cl.
USPC .............. 606/93; 604/191; 222/323; 222/391

(58) Field of Classification Search
USPC ............... 606/92–94; 222/323, 391; 604/191
See application file for complete search history.

(56) References Cited

U.S. PATENT DOCUMENTS

| | | | | |
|---|---|---|---|---|
| 2,869,543 A | | 8/1957 | Ratcliff et al. | |
| 3,141,583 A | * | 7/1964 | Mapel | 222/309 |
| 3,389,838 A | * | 6/1968 | Morra et al. | 222/630 |
| 3,894,663 A | * | 7/1975 | Carhart et al. | 222/309 |
| 3,985,122 A | * | 10/1976 | Topham | 600/578 |
| 4,090,639 A | * | 5/1978 | Campbell et al. | 222/43 |
| 4,188,949 A | * | 2/1980 | Antoshkiw | 604/191 |
| 4,364,388 A | * | 12/1982 | Cech | 604/224 |
| 4,476,866 A | * | 10/1984 | Chin | 606/194 |
| 4,526,303 A | * | 7/1985 | Harrod | 222/386.5 |
| 4,758,223 A | * | 7/1988 | Rydell | 604/97.02 |
| 4,994,065 A | * | 2/1991 | Gibbs et al. | 606/92 |
| 5,354,285 A | * | 10/1994 | Mazurik et al. | 604/191 |
| 5,431,654 A | * | 7/1995 | Nic | 606/92 |
| 5,501,374 A | * | 3/1996 | Laufer et al. | 222/391 |
| 5,512,054 A | * | 4/1996 | Morningstar | 604/191 |
| 5,638,997 A | * | 6/1997 | Hawkins et al. | 222/391 |
| 5,755,362 A | * | 5/1998 | Rodriguez et al. | 222/391 |

(Continued)

FOREIGN PATENT DOCUMENTS

| | | |
|---|---|---|
| EP | 0108584 | 1/1988 |
| EP | 1676538 | 7/2006 |
| WO | WO 2009156718 | 12/2009 |

*Primary Examiner* — Kevin C Sirmons
*Assistant Examiner* — William Carpenter
(74) *Attorney, Agent, or Firm* — G. Jo Hays; James Larson; James M. Pinkston (57) ABSTRACT

A system for harvesting, preparing, and delivering biological materials or other therapeutic agents is disclosed. The system is adaptable to a variety of biological materials or other therapeutic agents. The system is adaptable for minimally invasive procedures where access may be limited. The system includes provisions for delivering biological materials or other therapeutic agents along a curved path. The system is adaptable to maximize the delivered quantity of biological materials or other therapeutic agents, thus minimizing waste.

20 Claims, 9 Drawing Sheets

(56) References Cited

U.S. PATENT DOCUMENTS

| | | |
|---|---|---|
| 6,439,439 B1 * | 8/2002 | Rickard et al. ............... 222/391 |
| 6,457,606 B1 * | 10/2002 | Burke ............................. 222/1 |
| 6,672,489 B1 * | 1/2004 | Huang ........................ 222/391 |
| 7,252,671 B2 | 8/2007 | Scribner |
| 7,909,833 B2 * | 3/2011 | Voellmicke .................. 606/94 |
| 2007/0162042 A1 * | 7/2007 | Dunker et al. ................ 606/94 |
| 2009/0198183 A1 * | 8/2009 | Krumme et al. ............. 604/143 |
| 2009/0318925 A1 * | 12/2009 | Campion et al. .............. 606/93 |

* cited by examiner

BIOLOGICS DELIVERY SYSTEM

CROSS-REFERENCE TO RELATED APPLICATIONS

This application claims the benefit of the filing date of:

U.S. Provisional Patent Application No. 61/311,044, which was filed on Mar. 5, 2010, is entitled BIOLOGICS DELIVERY SYSTEM. The contents of U.S. Application No. 61/311,044 are hereby incorporated by reference as part of this application.

This application also claims the benefit of the filing date of:

U.S. Provisional Patent Application No. 61/389,626, which was filed on Oct. 4, 2010, is entitled SYSTEMS AND METHODS FOR INTRODUCING THERAPEUTIC AGENTS INTO A BONE CAVITY. The contents of U.S. Application No. 61/389,626 are hereby incorporated by reference as part of this application.

BACKGROUND OF THE INVENTION

Biological materials, or biologies, are used extensively in surgical situations to improve patient outcomes. Biologies are therapeutic agents that are derived from living organisms. Some examples of biologies include vaccines, blood and blood components, allergenics, somatic cells, stem cells, gene therapy, tissues, and recombinant therapeutic proteins created by biological processes. The physical properties of biologic materials, as well as some other therapeutic agents, make their delivery to a surgical site difficult, especially with a minimally invasive approach.

Most biologies delivery systems include a "caulking gun" style delivery unit. These units are capable of delivering material in a straight line-of-sight fashion. Furthermore, most delivery systems leave wasted material within the delivery system, such as within a nozzle or tip of the delivery system.

There is a need for a biologies delivery system that accepts a variety of biological materials. There is also a need for a biologies delivery system that is adapted for minimally invasive procedures. There is also a need for a biologies delivery system that is capable of delivering material to a surgical site via a curved path. The system also maximizes the delivered quantity of biological material, in other words, minimizing waste.

SUMMARY OF THE INVENTION

The present disclosure sets forth various embodiments of biologies delivery systems. The following is a partial list of some embodiments that fall within the scope of the present disclosure.

An embodiment of a system for delivering a biological material to a treatment site may include a chamber for containing the biological material, and a delivery apparatus for transferring the biological material from the chamber to the treatment site. The delivery apparatus may include a housing, an outer plunger extending through the housing, and a pawl. The pawl may include a tooth portion and a tab portion. The tab portion may extend outside the housing beside the outer plunger. The delivery apparatus may have a first configuration in which the tooth portion is biased toward the outer plunger, and a second configuration in which the tab portion is urged toward alignment with the outer plunger to temporarily overcome the bias.

In another embodiment, the delivery apparatus may transfer substantially all of the biological material from the chamber to the host site.

In yet another embodiment, the delivery apparatus may include an inner plunger that slides within the outer plunger. The delivery apparatus may have a third configuration in which the tooth portion is biased toward the inner plunger, and a fourth configuration in which the tab portion is urged toward alignment with the inner plunger to temporarily overcome the bias.

In yet another embodiment, the chamber may include a compartment for containing the biological material, and a tube extending from the compartment. The outer plunger may slide within the compartment and the inner plunger may slide within the tube.

In yet another embodiment, the tube and the inner plunger may have a fixed radius of curvature.

In yet another embodiment, the tube and the inner plunger may have a variable radius of curvature In yet another embodiment, when the outer plunger slides within the compartment, substantially all of the biological material may be transferred from the compartment to the tube, and when the inner plunger slides within the tube, substantially all of the biological material may be transferred from the tube to the host site.

In yet another embodiment of a system for delivering a biological material to a host site, the system may include a compartment for containing the biological material, a tube extending from the compartment along a curved path, and a delivery apparatus for transferring the biological material from the compartment through the tube along the curved path to the host site, The delivery apparatus may include an inner plunger that slides within the tube along the curved path.

In yet another embodiment, the delivery apparatus may transfer substantially all of the biological material from the compartment to the host site.

In yet another embodiment, the tube and the inner plunger may have a fixed radius of curvature.

In yet another embodiment, the tube and the inner plunger may be flexible.

In yet another embodiment, the delivery apparatus may include an inner plunger shield covering a first end of the inner plunger. The inner plunger shield may slide within the tube ahead of the inner plunger.

In yet another embodiment, the delivery apparatus may include an outer plunger that slides within the compartment. The inner plunger may slide within the outer plunger.

In yet another embodiment, the delivery apparatus may include an outer plunger shield covering a first end of the outer plunger. The outer plunger shield may slide within the compartment ahead of the outer plunger.

In yet another embodiment, the compartment may extend along the curved path. The outer plunger may slide within the compartment along the curved path.

An embodiment of a method of delivering a biological material to a host site may include providing a delivery instrument, where the delivery instrument may include a compartment and a tube extending from the compartment along a curved path and terminating in an open tip; placing the biological material in the compartment; positioning the open tip of the tube at the host site; transferring substantially all of the biological material from the chamber through the tube along the curved path to the host site; and withdrawing the open tip of the tube from the host site.

In another embodiment, the delivery instrument may include an outer plunger that slides within the compartment and an inner plunger that slides within the outer plunger and the tube. Transferring substantially all of the biological material from the chamber to the host site may include sliding the outer plunger within the compartment to transfer substantially all of the biological material from the compartment to the tube and sliding the inner plunger within the tube to transfer substantially all of the biological material from the tube to the host site.

In yet another embodiment, placing the biological material in the compartment may include inserting a packet containing the biological material into the compartment.

In yet another embodiment, the packet may include a plurality of separate chambers, where each chamber may contain a different component of the biological material.

In yet another embodiment, the method may include sealing the biological material in the packet before inserting the packet into the compartment.

In yet another embodiment, the method may include breaching the sealed packet before transferring substantially all of the biological material from the chamber through the tube along the curved path to the host site.

DETAILED DESCRIPTION

While certain embodiments have been shown and described in detail below, it will be clear to the person skilled in the art upon reading and understanding this disclosure that changes, modifications, and variations may be made and remain within the scope of the systems, kits, components, and methods described herein. Furthermore, while various features are grouped together in the embodiments for the purpose of streamlining the disclosure, it is appreciated that features from different embodiments may be combined to form additional embodiments which are all contemplated within the scope of the present disclosure.

The following description and accompanying drawings are offered by way of illustration only. In particular, while the present disclosure sets forth an embodiment in the context of delivering biological materials, one of skill in the art will appreciate that the components, systems, kits, and methods may be applicable to delivery of other materials of medical interest, such as structural agents like bone cement, or therapeutic agents like antibiotics or osteoconductive materials.

Not every feature of each embodiment is labeled in every figure in which that embodiment appears, in order to keep the figures clear. Similar reference numbers (for example, those that are identical except for the first numeral) are used to indicate similar features in different embodiments.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. These descriptive terms may be applied to an animate or inanimate body.

Referring to FIGS. 1-7, a delivery instrument 100 may include a dual plunger ratcheting handle 200 and a delivery chamber 300. Delivery chamber 300 may be removably fixed to handle 200.

The ratcheting handle 200 may include a first stationary body 202, a second stationary body 204, an actuating handle 206, a ratcheting mechanism 208, and concentrically nested telescoping outer and inner plungers 210 and 212, respectively. Ratcheting handle 200 may be described as a dispensing apparatus or delivery apparatus. Ratcheting handle 200 may be used to transfer the biological material from the delivery chamber 300 to a host site.

The first and second stationary bodies 202, 204 may fit together to form a housing 224 with a protruding stationary handle 226. First and second stationary bodies 202, 204 may be at least partial mirror images of each other, as can be appreciated from FIGS. 2-6. When the ratcheting handle 200 is fully assembled, the first and second stationary bodies 202, 204 may enclose portions of the actuating handle 206, the ratcheting mechanism 208, and/or the outer and inner plungers 210 and 212.

Figure 1:
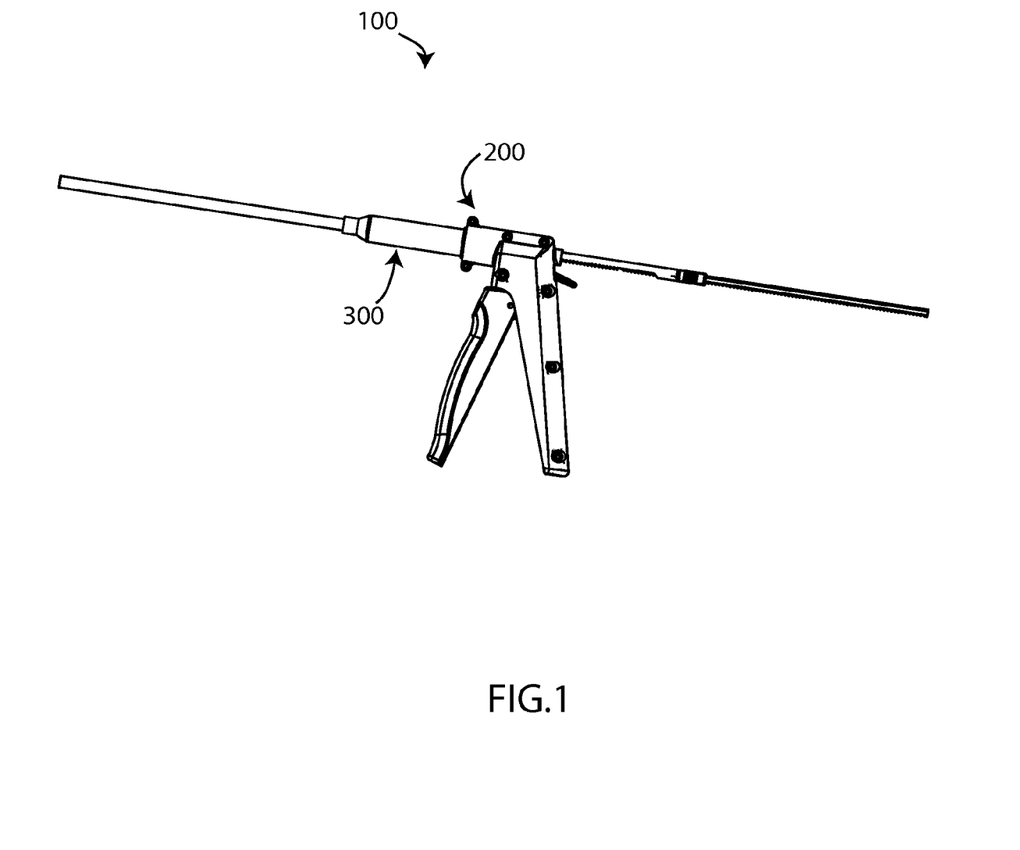
FIG. 1 is a side view of a delivery instrument.
Figure 2:
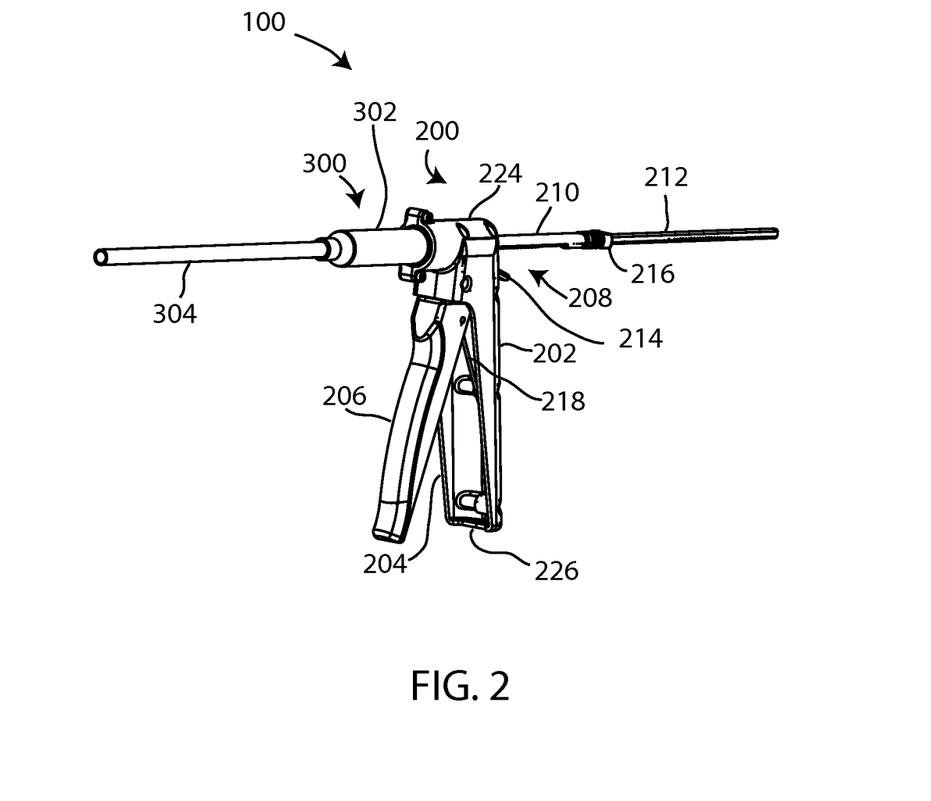
FIG. 2 is a front perspective view of the delivery instrument of FIG. 1.
Figure 3:
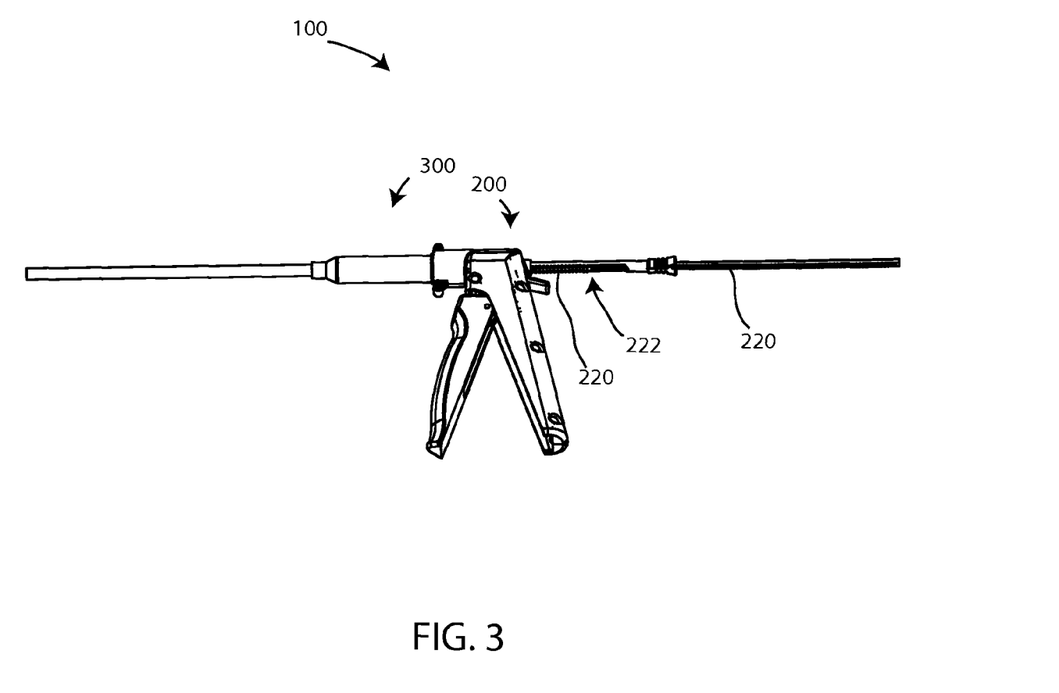
FIG. 3 is a side perspective view of the delivery instrument of FIG. 1.
Figure 4:
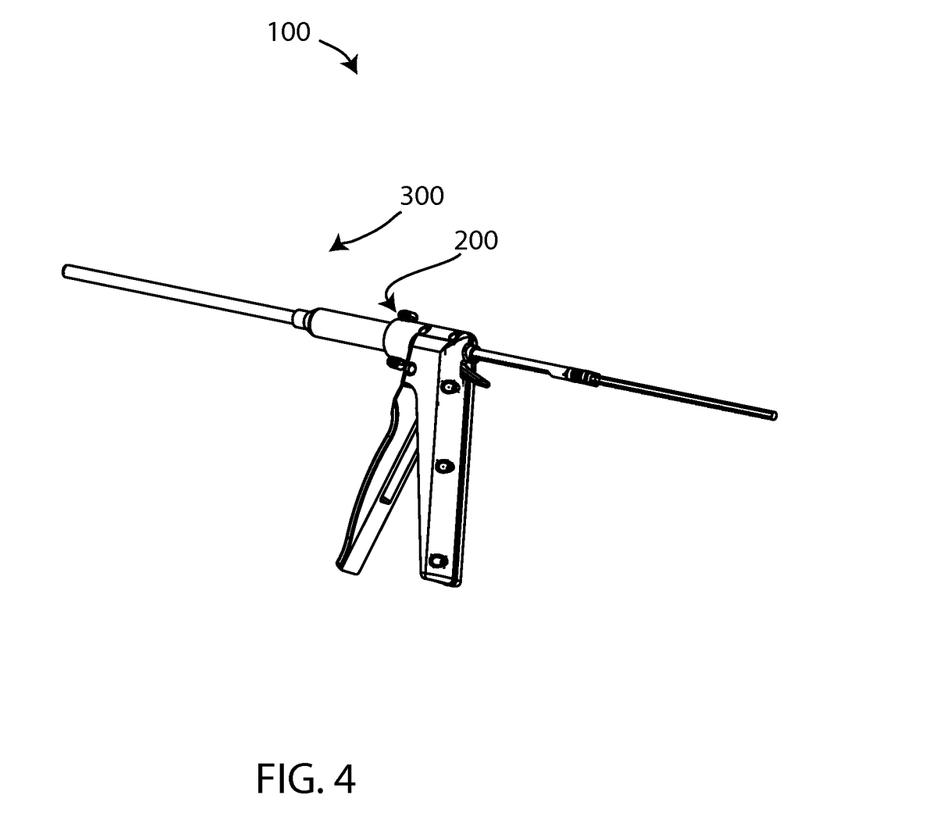
FIG. 4 is a back perspective view of the delivery instrument of FIG. 1.
Figure 5:
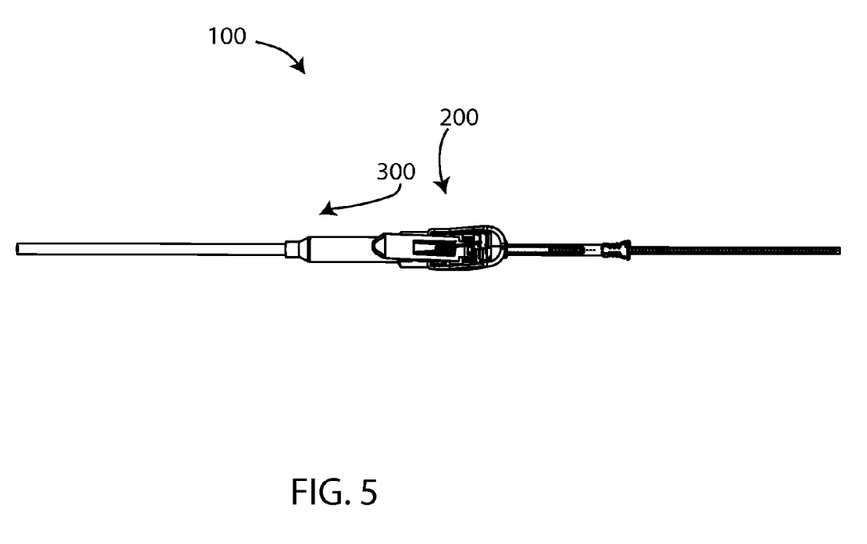
FIG. 5 is a bottom view of the delivery instrument of FIG. 1.
Figure 6:
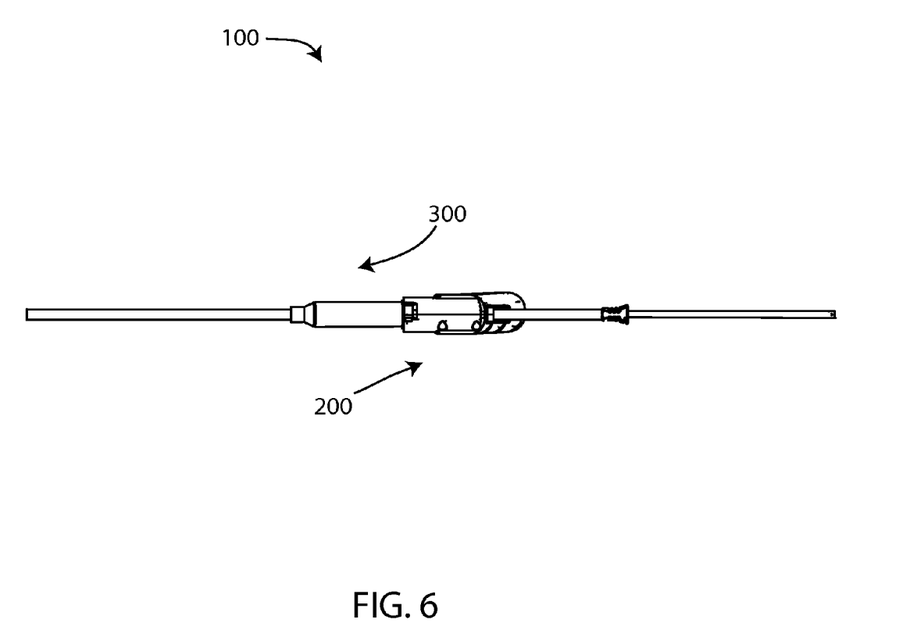
FIG. 6 is a top view of the delivery instrument of FIG. 1.
Figure 7:
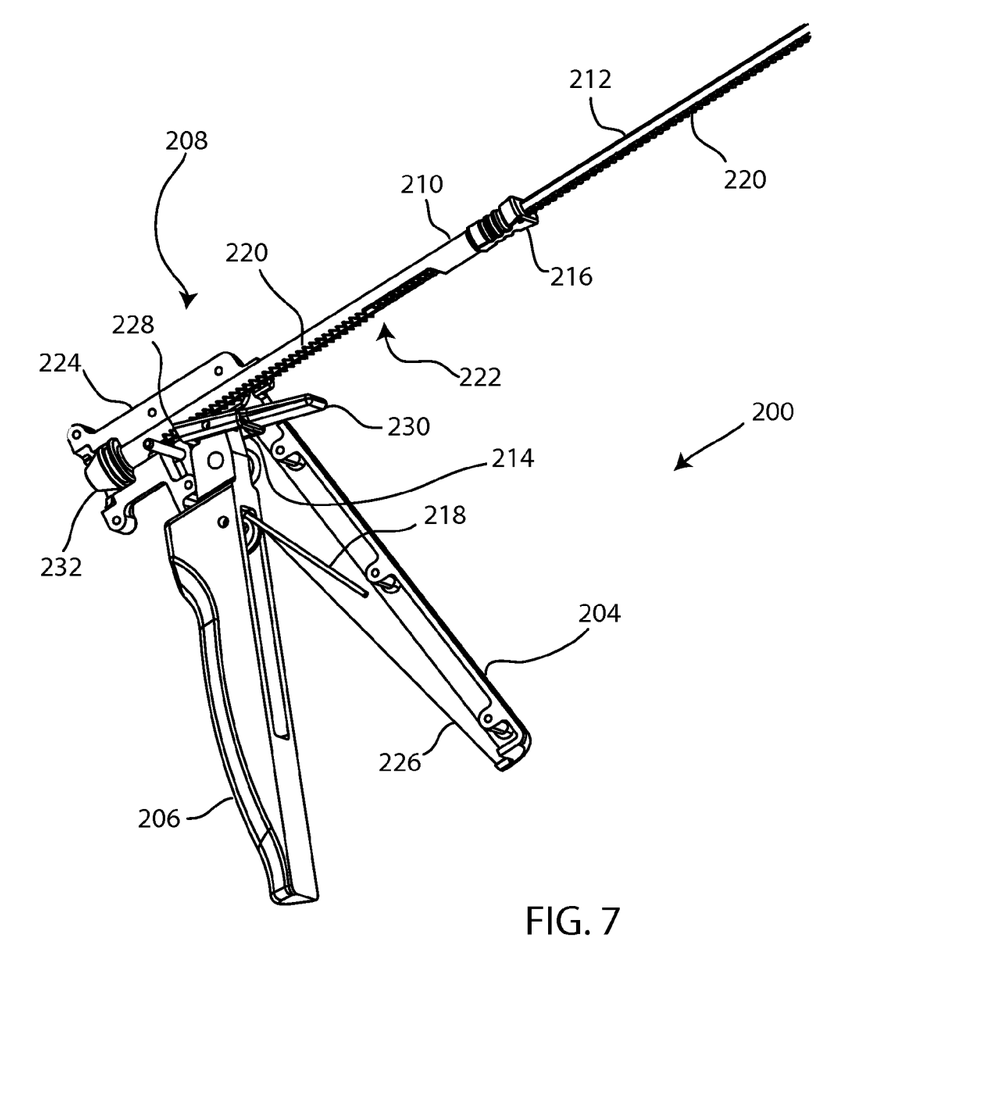
FIG. 7 is a side perspective view of the delivery instrument of FIG. 1, with a first stationary body and a delivery chamber removed to show inner components of the delivery instrument.

The actuating handle 206 may be connected between, and hinged to, the first and second stationary bodies 202, 204, as may be seen in FIGS. 2 and 7. The actuating handle 206 may be described as a movable handle because it can move relative to the stationary bodies 202, 204 in use. The actuating handle 206 may be biased to stand away from the stationary handle 226 except when a user squeezes the actuating handle 206 toward the stationary handle 226. For example, spring 218 may bias actuating handle 206.

The ratcheting mechanism 208, which may be seen best in FIG. 7, may include lever 214. Lever 214 may be described as a pawl. Lever 214 may be hinged to actuating handle 206. Lever 214 may have a front tooth portion 228 on one side of the hinge and a rear tab portion 230 on an opposite side of the hinge. It can be appreciated from FIG. 7 that tab portion 230 of lever 214 may extend outside the housing 224 beside the outer and inner plungers 210, 212 when the ratcheting handle 200 is fully assembled. When the ratcheting handle 200 is fully assembled, lever 214 may be biased to press against the outer and/or inner plungers 210, 212 so that tooth portion 228 of lever 214 may engage grooves 220 on the outer and inner plungers 210, 212, except when a user lifts tab portion 230 of lever 214, thus urging tab portion 230 toward alignment with the outer and/or inner plungers 210, 212. For example, a spring (not shown) may bias lever 214 against the plungers 210, 212. Ratcheting handle 200 may thus have a first configuration, in which the tooth portion 228 is biased toward the outer plunger 210; a second configuration, in which the tab portion 230 is urged toward alignment with the outer plunger 210; a third configuration, in which the tooth portion 228 is biased toward the inner plunger 212; and a fourth configuration, in which the tab portion 230 is urged toward alignment with the inner plunger 212.

Outer and inner plungers 210, 212 may include shafts which are slidably supported through a portion of the housing 224. Inner plunger 212 may slide within outer plunger 210 in a telescoping manner. Outer plunger 210 may include a slot or window 222 which exposes a portion of inner plunger 212, as may be seen in FIGS. 3 and 7. In the third and fourth configurations of the ratcheting handle 200, the outer plunger 210 may be forwardly positioned so that the tooth portion 228 of lever 214 reaches through window 222 to engage inner plunger 212. It can be appreciated that lever 214 may engage grooves 220 to propel the outer or inner plunger 210, 212 forward as the actuating handle 206 is alternately squeezed toward the first and second stationary bodies 202, 204 and released. It can also be appreciated that outer plunger 210 may advance until the lever 214 encounters a final groove 220, at which point lever 214 may engage an initial groove 220 on inner plunger 212, thus advancing inner plunger 212.

Figure 8:
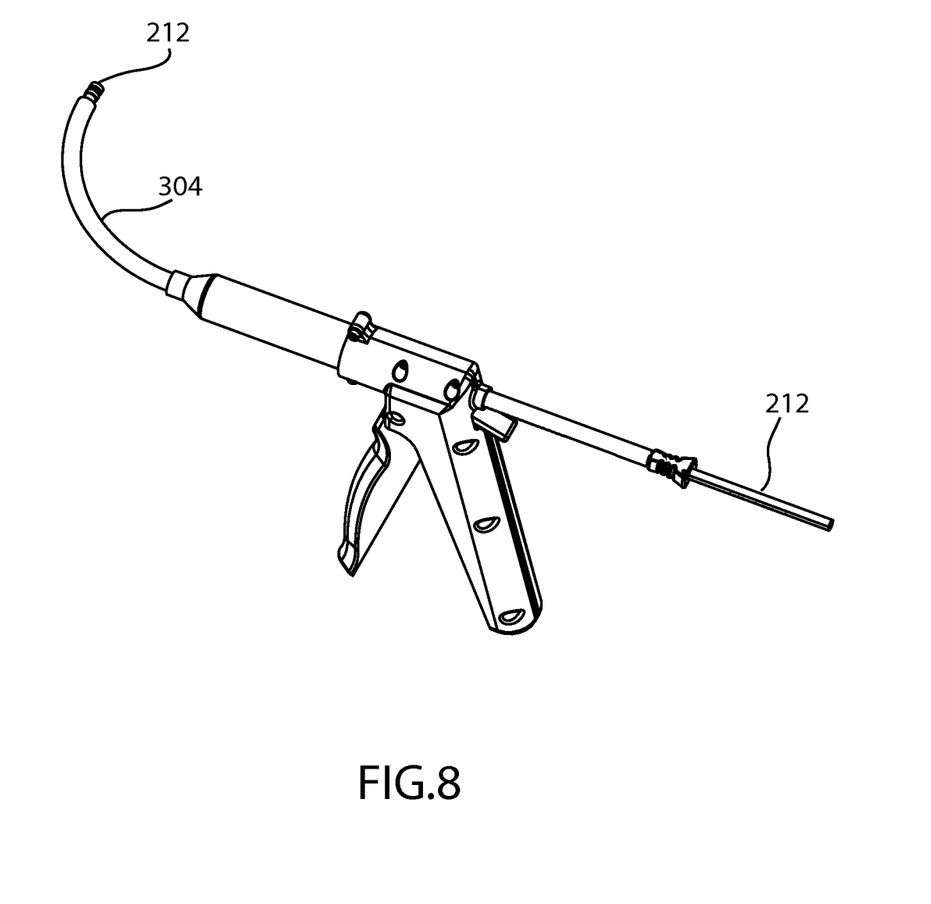
FIG. 8 is a side perspective view of another embodiment of a delivery instrument.
Figure 9:
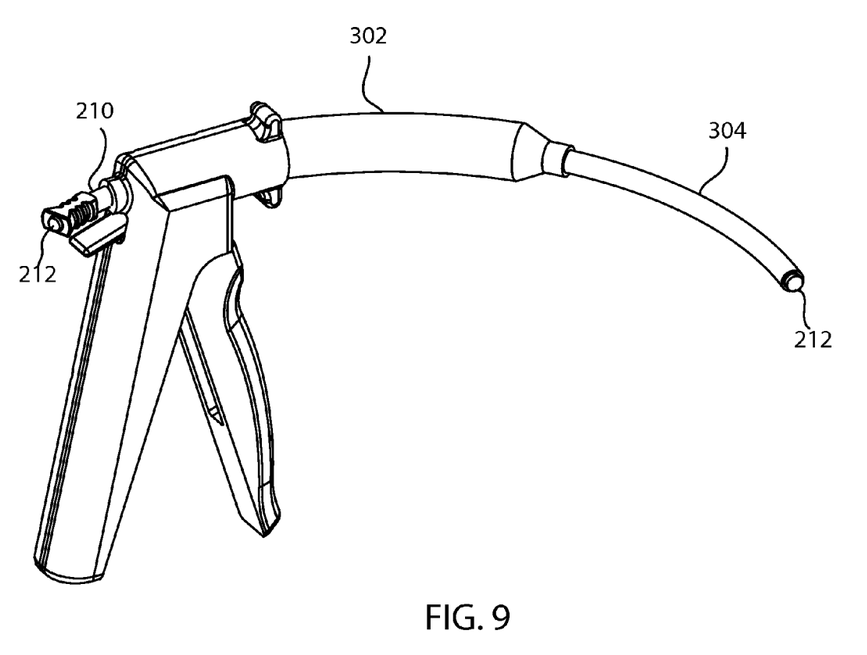
FIG. 9 is a side perspective view of yet another embodiment of a delivery instrument.

The delivery chamber 300 may include a main compartment 302 with an attached length of delivery tubing 304 extending from the compartment 302, as may be seen in FIG. 2. Delivery chamber 300 may be described as a syringe, cartridge, capsule, cassette, packet, or pod. Delivery chamber 300 may contain the biological material. The main compartment 302 may contain, or be filled with, a desired amount of biologies material. The delivery tube 304 may have a fixed shape, which may follow a curved path (as in FIGS. 8-9), or be straight (as in FIGS. 1-7) or bent. Alternatively, the delivery tube 304 may be bendable or flexible, allowing the biological material to be delivered around a variable radius bend or curve in the tube 304. The inner plunger 212 may have a corresponding fixed shape, or may be bendable or flexible to complement the delivery tube 304. For example, at least a portion of the inner plunger 212 may be a spiral wound cable shaft or may include multiple segments hinged together. FIGS. 1-7 illustrate a straight inner plunger 212 corresponding to the straight tube 304. FIGS. 8-9 illustrate an inner plunger 212 which follows a curved path corresponding to the curved tube 304. Similarly, the main compartment 302 and the outer plunger 210 may be fixed, bendable, or flexible. FIGS. 1-7 illustrate an outer plunger 210 and main compartment 302 which are straight, and FIGS. 8-9 illustrate an outer plunger 210 and main compartment 302 which follow a curved path. These are some examples of ways that the present system may provide a biologies delivery system that is capable of delivering material to a surgical site via a curved path. These are also some examples of ways that the present system may provide a biologies delivery system that is adapted for minimally invasive procedures.

The delivery instrument 100 may be designed so that outer plunger 210 slides within main compartment 302 to push the biological material from the main compartment 302 to the tube 304, and inner plunger 212 slides within tube 304 to push the biological material from the tube 304 to the host site. The relative dimensions of various components of the delivery instrument 100 may be selected so that lever 214 encounters a final groove 220 on outer plunger 210 as outer plunger 210 finishes pushing substantially all of the biological material from main compartment 302. Furthermore, the relative dimensions of various components of the delivery instrument 100 may be selected so that lever 214 encounters a final groove 220 on inner plunger 212 as inner plunger 212 finishes pushing substantially all of the biological material from tube 304. Alternatively, lever 214 may encounter a penultimate groove 220, or another groove 220, instead of a final groove 220 in the above scenarios.

The delivery chamber 300 may also include one or more plunger shields 232 to protect the plungers 210, 212 from contamination by the biologic material. The plunger shields 232 may be dimensioned to fit firmly within corresponding portions of the delivery chamber 300, and may include compliant portions or rim flanges so that the plunger shields 232 may provide a seal within the delivery chamber 300. The plunger shields 232 may act as pistons within the delivery chamber 300. A plunger shield 232 for the outer plunger 210 may slide within the main compartment 302 ahead of the outer plunger 210. A plunger shield 232 for the inner plunger 212 may slide within the delivery tubing 304 ahead of the inner plunger 212. The inner plunger shield 232 may also slide through the main compartment 302, although there may not be a tight fit, or even contact, between the inner plunger shield 232 and the main compartment 302. A single plunger shield 232 may cover the plungers 210, 212, and may include a central break-away portion that separates from the remaining plunger shield 232 when the inner plunger 212 advances past the outer plunger 210. In another example, separate plunger shields 232 may be provided. The plunger shield 232 for the outer plunger 210 may be between the plunger shield 232 for the inner plunger 212 and the outer plunger 210. The plunger shield 232 may be reusable or disposable.

The delivery chamber 300 may be attached to the ratcheting handle 200 with a mechanical connection such as threads, snap fit, bayonet connection or other method of coupling. The mechanical connection between the delivery chamber 300 and the ratcheting handle 200 may be a proprietary interface. An example of a proprietary interface that may be adapted for use between the delivery chamber 300 and the ratcheting handle 200 may be found in U.S. patent application Ser. No. 12/943,586, which is incorporated herein by reference in its entirety. One example of a way in which the interface, or interconnection, of U.S. patent application Ser. No. 12/943,586 may be adapted for use between the delivery chamber 300 and the ratcheting handle 200 is to form a protruding structure like shaft 12 on portions of the first and second stationary bodies 202, 204, and a recessed structure like socket 62 on a portion of the main compartment 302.

When the ratcheting handle 200 is fully assembled and actuated, the nested plungers 210, 212 may advance forward together until the outer plunger 210 has transferred the charge of biological material from the main compartment 302 into the delivery tube 304. During this step, a portion of the biological material may pass out of the delivery tube 304 to the host site, which may be a treatment site or a site of damaged tissue, such as bone necrosis. Once the outer plunger 210 has bottomed inside the main compartment 302, the inner plunger 212 may advance alone through the delivery tube 304 to transfer the biological material from the delivery tube 304 to the host site. In this manner, the system may fully evacuate biologic material from the delivery chamber 300, whether or not a mixing insert is present in the delivery chamber 300. These are some examples of ways that the present system may maximize the delivered quantity of biological material, or in other words, minimize the wasted quantity of biological material.

After the charge of biological material has been delivered, both outer and inner plungers 210, 212 may be retracted back to their starting positions by holding lever 214 up while pulling on knob 216. The delivery chamber 300 may be replaced or reloaded to deliver additional charges of biological material.

Methods of harvesting, preparing, and delivering biological materials or other therapeutic agents will now be described. The systems disclosed herein may deliver materials such as bone-graft-based materials, putties, bone cement, and the like. It is contemplated that the procedural steps set forth below may be combined in an a-la-carte manner to provide several methods within the scope of the present disclosure.

Biological materials may be harvested from a donor site. For example, bone marrow may be harvested from a donor site in a patient's ilium, or blood plasma may be harvested from a patient's circulatory system. Biological materials may derive from other sources besides donor sites in the patient's own body.

The biological materials may require some preparation in order to provide the desired therapeutic effect. For example, harvested material may require washing, purification, activation, or concentration. In another example, a portion of cancellous bone may be ground in a bone mill, mixed with a solvent or diluent, and/or spun in a centrifuge in order to segregate desired bone marrow constituent material for use in a host site. In yet another example, the biological material may include a plurality of constituents which may be mixed immediately prior to use. Mixing may be done in a bowl with a spatula. The system may include a bone mill, spatula, funnel, reagents, therapeutic agents, and/or additives to facilitate preparation of the biological material.

The biological materials may be loaded into a delivery system for delivery to a host site. In one example, a system may include pre-packed, modular, and/or disposable units which contain biological materials or other therapeutic agents. For example, a unit may be a syringe, cartridge, capsule, cassette, packet, pod, or chamber. In another example, a unit may be the delivery chamber 300 described above. The unit may be a separate container or packet which is insertable within the delivery chamber 300. The biological materials or other therapeutic agents may be substantially sealed within the unit until the time of delivery to a host, or recipient, site. In other words, the unit may be charged with a dose of biological material. The unit may be breached at the time of delivery before transferring the biological material to the host site. Some examples of ways the unit may be breached include removing a removable seal, flap, cap, cover, or plug; breaking or tearing a frangible or rupturable portion; or piercing a membrane, wall, or diaphragm.

Some biological materials or other therapeutic agents may include a plurality of components which may be kept separate until the time of delivery to the host site. Therefore, in another example, a system may include mixing units having multiple separate chambers, each chamber containing a different component of the final biologic material. The mixing units may incorporate one or more attributes of the units described in the preceding paragraph. The separate components may mix as the components pass from the separate chambers to the host site. For example, turbulent flow between the chambers and the host site may adequately mix the separate components. A mixing unit may optionally include a means for mixing the separate components. The means for mixing may be described as a mixing insert, for example, a helical insert. The means for mixing may split and combine streams of material from each chamber in order to mix the separate components. The streams may be repeatedly split and combined to ensure thorough mixing.

In yet another example, a system may include units which may be filled with biological materials or other therapeutic agents by the user. These units may be advantageous in the situation where biological materials are harvested from a donor site and prepared intraoperatively. The units may incorporate one or more attributes of the units described in the preceding two paragraphs, in a design that permits at least temporary access to the chamber or chambers of the unit in order to fill the unit.

A single system may include pre-packed units, mixing units, and/or user-fillable units. These are some examples of ways that the present system may provide a biologies delivery system that accepts a variety of biological materials.

A host site may be prepared in a variety of ways. The following are some examples of ways that a host site may be prepared within a bone. U.S. Provisional Patent Application No. 61/389,626, which is incorporated herein by reference in its entirety, provides additional disclosure of instruments and methods for preparing a host site in a bone. Any of the host site preparation methods set forth below may be adapted for use along a straight or curved pathway.

In one example, an instrument may include a flexible loop within an outer tube. The loop may flex into a narrow configuration in order to fit within the tube, and may flex into a wide configuration once the loop is moved out of the tube. The loop may include cutting blades, wires, or ribbons. Multiple loops may be provided in a three-dimensional (3D) array. The loops may be of different sizes or profiles. The loop or loops may be steerable so that the loop or loops can be bent to extend well beyond the outside diameter of the tube. By rotating the loop or loops, cancellous bone at the host site may be broken up and removed to form a bone cavity. Morselized bone may be removed by suction through the tube. The tube may also deliver an irrigation solution counterflow to flush the host cavity as it is being formed. The instrument may also include a drill tip mounted on a leading end of the loop or cutting ribbons.

In yet another example, an instrument may include a rigid suction tube with an articulated tip. In this example, the instrument may remove bone directly with suction alone. The tip of the instrument may articulate with respect to a main shaft of the instrument, so that the tip may pivot to reach beyond the outer diameter of the shaft.

In yet another example, an instrument may include a plurality of flexible wires or brush filaments that are extendably stowed within an outer tube. Upon extending the wires from the tube, the wires may diverge spontaneously. The wires may also diverge due to rotation of an inner shaft to which the wires are coupled. As the inner shaft rotates, the wires sweep bone from the walls of the developing cavity. Suction through the outer tube may remove morselized bone bits. Irrigation fluid may also be delivered through the outer tube in counter flow to the suction.

In another example, a suction curette may be provided to scoop bone toward an integral suction inlet. The curette tip may articulate so that the curette may pivot with respect to the main instrument shaft.

In another example, an instrument may push bone peripherally to create a host cavity. The instrument may carry a balloon or basket at its tip. The basket may be urged from a relaxed configuration to an expanded configuration to push softer cancellous bone laterally or peripherally.

In yet another example, an instrument may include jaws mounted at a working end of the instrument. The jaws may be closed to present a low profile for insertion of the instrument to the desired host location. The jaws may then be opened to present a larger profile, and the instrument rotated to cut a cavity. Opposed outer surfaces of the jaws may include cutting flutes or sharp edges. Suction may remove debris along the shaft of the instrument.

Once a host site is prepared, the delivery instrument 100 with biological materials may be introduced into the host site. For example, an open tip of the delivery tubing 304 may be positioned at the host site. Actuation of the delivery instrument 100 may deliver substantially all of the biological material to the host site. After delivery of the biological material is complete, the delivery instrument may be withdrawn and the surgical wound closed.

In yet another example, an integrated system may be provided for forming and filling a bone cavity. The system may include a cannula, a trocar, a syringe, a drill, and a driver. The trocar may be inserted into the cannula, and both components may be introduced to the desired host location or entry site on a bone surface. The trocar may be removed. The drill may be operatively coupled to a driver, and the drill inserted through the cannula to the host location or entry site. A hole may be drilled to a location within the bone. Irrigation and/or suction may be provided through lumens in the drill and/or cannula during the drilling step to flush bone chips from the host location. The drill may be left in place while the driver is uncoupled from the drill and the syringe is attached to the drill. The syringe may be preloaded with a therapeutic agent, such as bone marrow concentrate. The syringe may be a delivery chamber 300 as described above. The syringe may be operatively coupled to a delivery handle 200 as described above. The concentrate may be injected to the host site through the drill and/or cannula lumens. The drill may then be turned in reverse to pack the therapeutic agent into the cancellous interstices. Additional concentrate may be injected as the drill is withdrawn, so that the cavity and drill tract are filled with concentrate.

While the present disclosure has been made in the context of a delivery system for biological materials, the systems and methods described herein have a broad range of applications. By way of non-limiting example, the systems and methods may be applicable to other therapeutic agents or structural materials.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features.

Furthermore, a device or structure that is configured in a certain way is configured in at least that way, but may also be configured in ways that are not listed.

The invention claimed is:

1. A system for delivering a biological material to a treatment site, the system comprising:
   a chamber for containing the biological material; and
   a delivery apparatus for transferring the biological material from the chamber to the treatment site, the delivery apparatus comprising:
   a housing;
   an outer plunger extending through the housing;
   an inner plunger, wherein the inner plunger slides within the outer plunger; and
   a pawl, wherein the pawl comprises a tooth portion and a tab portion, wherein the tab portion extends outside the housing beside the outer plunger;
   wherein the delivery apparatus comprises:
   a first configuration in which the tooth portion is biased toward the outer plunger,
   a second configuration in which the tab portion is urged toward alignment with the outer plunger to temporarily overcome the bias,
   a third configuration in which the tooth portion is biased toward the inner plunger, and
   a fourth configuration in which the tab portion is urged toward alignment with the inner plunger to temporarily overcome the bias.

2. The system of claim 1, wherein the delivery apparatus transfers substantially all of the biological material from the chamber to the host site.

3. The system of claim 1, wherein the chamber comprises:
   a compartment for containing the biological material; and
   a tube extending from the compartment;
   wherein the outer plunger slides within the compartment;
   wherein the inner plunger slides within the tube.

4. The system of claim 3, wherein
   when the outer plunger slides within the compartment, substantially all of the biological material is transferred from the compartment to the tube; and
   when the inner plunger slides within the tube, substantially all of the biological material is transferred from the tube to the host site.

5. The system of claim 3, wherein the delivery apparatus comprises:
   an outer plunger shield covering a first end of the outer plunger, wherein the outer plunger shield slides within the compartment ahead of the outer plunger.

6. The system of claim 3, wherein the delivery apparatus comprises:
   an inner plunger shield covering a first end of the inner plunger, wherein the inner plunger shield slides within the tube ahead of the inner plunger.

7. The system of claim 1, wherein the outer plunger comprises a window, wherein, in the third configuration, the tooth portion reaches through the window to engage the inner plunger.

8. A system for delivering a biological material to a host site, the system comprising:
   a compartment for containing the biological material;
   a tube extending from the compartment along a path; and
   a delivery apparatus for transferring the biological material from the compartment through the tube along the path to the host site, the delivery apparatus comprising:
   an outer plunger, wherein the outer plunger slides within the compartment;

an inner plunger, wherein the inner plunger slides within the outer plunger, wherein the inner plunger slides within the tube along the path; and a pawl, wherein the pawl comprises a tooth portion and a tab portion, wherein the tab portion extends beside at least one of the outer plunger and the inner plunger;

wherein the delivery apparatus comprises a first configuration, in which the tooth portion is biased to engage at least one of the outer plunger and the inner plunger, a second configuration, in which the bias is temporarily overcome and the tab portion is urged toward alignment with at least one of the outer plunger and the inner plunger, a third configuration in which the tooth portion is biased toward the inner plunger, and a fourth configuration in which the tab portion is urged toward alignment with the inner plunger to temporarily overcome the bias.

9. The system of claim 8, wherein the delivery apparatus transfers substantially all of the biological material from the compartment to the host site.

10. The system of claim 8, wherein the delivery apparatus comprises:
an inner plunger shield covering a first end of the inner plunger, wherein the inner plunger shield slides within the tube ahead of the inner plunger.

11. The system of claim 8, wherein the delivery apparatus comprises:
an outer plunger shield covering a first end of the outer plunger, wherein the outer plunger shield slides within the compartment ahead of the outer plunger.

12. The system of claim 8, wherein the compartment extends along the path; wherein the outer plunger slides within the compartment along the path.

13. The system of claim 8, wherein the delivery apparatus comprises a housing, wherein the outer plunger extends through the housing, wherein the tab portion extends outside the housing.

14. A system for delivering a biological material to a treatment site, the system comprising:
a chamber that receives the biological material;
a tube extending from the chamber along a path; and
a delivery apparatus comprising:
a housing;
telescoping outer and inner plungers that extend through the housing and slide within the chamber; and
a pawl comprising a tooth portion and a tab portion, wherein the tab portion extends outside the housing;

wherein the chamber comprises a connection portion opposite the tube, wherein the connection portion couples the chamber to the housing;
wherein the tooth portion engages grooves on the outer plunger to propel the outer and inner plungers forward together from the connection portion toward the tube until the outer plunger bottoms out inside the chamber;
wherein, after the outer plunger bottoms out inside the chamber, the tooth portion engages grooves on the inner plunger to propel the inner plunger forward alone from the chamber through the tube;
wherein the delivery apparatus comprises:
a first configuration in which the tooth portion is biased to press against at least one of the outer and inner plungers, and
a second configuration in which the bias is temporarily overcome and the tab portion is urged toward alignment with the outer and inner plungers.

15. The system of claim 14, wherein
the outer plunger comprises a window that exposes a portion of the inner plunger;
wherein, when the outer plunger bottoms out inside the chamber, the tooth portion reaches through the window to engage the grooves on the inner plunger.

16. The system of claim 14, comprising an outer plunger shield which fits within the chamber and slides within the chamber ahead of the outer plunger as the outer plunger slides from the connection portion toward the tube.

17. The system of claim 16, comprising an inner plunger shield which fits within the tube and slides within the tube ahead of the inner plunger as the inner plunger slides from the chamber through the tube.

18. The system of claim 17, wherein the outer plunger shield is between the outer plunger and the inner plunger shield.

19. The system of claim 14, wherein the delivery apparatus comprises:
a third configuration in which the tooth portion is biased toward the inner plunger.

20. The system of claim 19, wherein the delivery apparatus comprises:
a fourth configuration in which the tab portion is urged toward alignment with the inner plunger to temporarily overcome the bias.

* * * * *